United States Patent
Zhang et al.

(10) Patent No.: US 9,918,956 B2
(45) Date of Patent: Mar. 20, 2018

(54) CHLOROGENIC ACID POWDER-INJECTION AND PREPARATION METHOD THEREOF

(71) Applicant: SICHUAN JIUZHANG BIOLOGICAL SCIENCE AND TECHNOLOGY CO., LTD, Chengdu, Sichuan (CN)

(72) Inventors: Jie Zhang, Sichuan (CN); Huarong Yang, Sichuan (CN); Chenxu Tian, Sichuan (CN); Yongjiang Yan, Sichuan (CN); Lina Zhu, Sichuan (CN); Wang Huang, Sichuan (CN)

(73) Assignee: SICHUAN JIUZHANG BIOLOGICAL SCIENCE AND TECHNOLOGY CO., LTD, Chengdu, Sichuan (CN)

( * ) Notice: Subject to any disclaimer, the term of this patent is extended or adjusted under 35 U.S.C. 154(b) by 3 days.

(21) Appl. No.: 14/911,100

(22) PCT Filed: Aug. 21, 2013

(86) PCT No.: PCT/CN2013/081967
§ 371 (c)(1),
(2) Date: Feb. 9, 2016

(87) PCT Pub. No.: WO2015/024217
PCT Pub. Date: Feb. 26, 2015

(65) Prior Publication Data
US 2016/0193176 A1    Jul. 7, 2016

(51) Int. Cl.
A61K 31/235 (2006.01)
A61K 31/25 (2006.01)
A61K 9/19 (2006.01)
A61K 31/216 (2006.01)
A61K 9/00 (2006.01)
A61K 47/20 (2006.01)
A61K 47/26 (2006.01)

(52) U.S. Cl.
CPC ............ *A61K 31/25* (2013.01); *A61K 9/0019* (2013.01); *A61K 9/19* (2013.01); *A61K 31/216* (2013.01); *A61K 47/20* (2013.01); *A61K 47/26* (2013.01)

(58) Field of Classification Search
CPC ........ A61K 31/25; A61K 9/0019; A61K 9/19; A61K 31/216; A61K 47/20; A61K 47/26
See application file for complete search history.

(56) References Cited

FOREIGN PATENT DOCUMENTS

| CN | 1568960 A | 1/2005 |
|---|---|---|
| CN | 1616403 A | 5/2005 |
| CN | 1813705 A | 8/2006 |
| CN | 102391119 A | 3/2012 |

OTHER PUBLICATIONS

Liu (CN1813705A, published Aug. 9, 2006, Machine Translation).*
Lin et al (Shipin Gongye Keji, 2000, 21(2), 20-22, SciFinder Scholar Abstract translation).*
Liu (CN1813705A, published Aug. 9, 2006, cited and submitted by the Applicants in the instant application, Machine Translation).*
Lin et al (Huaxi Yaoxue Zazhi, 2005, 20(3), 225-227, Machine Translation).*
Lin et al (Huaxi Yaoxue Zazhi, 2005, 20(3), 225-227, Chinese).*

* cited by examiner

*Primary Examiner* — Kortney L Klinkel
*Assistant Examiner* — Ibrahim D Bori
(74) *Attorney, Agent, or Firm* — Novick, Kim & Lee, PLLC; Allen Xue

(57) ABSTRACT

The present invention provides a chlorogenic acid powder-injection. The chlorogenic acid powder-injection is prepared from the following raw materials in parts by weight: 1-120 parts of chlorogenic acid, 1-320 parts of a bracket agent and 1-8 parts of an antioxidant. The present invention further provides a preparation method of the powder-injection. The chlorogenic acid powder-injection provided in the present invention is good in stability, strong in re-solubility and safe in clinical use.

14 Claims, 3 Drawing Sheets

CHLOROGENIC ACID POWDER-INJECTION AND PREPARATION METHOD THEREOF

FIELD OF TECHNOLOGY

The present invention relates to chlorogenic acid powder for injection.

BACKGROUND

Chlorogenic acid is a polyphenol compound, and the experiments have shown chlorogenic acid is not stable in the presence of acids, bases, light and high temperature. Hong-Hao Zhou, Olthof M R, Gonthir M P, et al. reported that chlorogenic acid, belonging to instable polyphenolic compounds, is susceptible to effects of intestinal bacteria and so on, and thus oral administration of chlorogenic acid showed a lower biological availability, and it is better to choose blood vessel administration. As a result, injections are a better dosage for this drug. Considering that chlorogenic acid is not stable in aqueous solution, it is not suitable to use its liquid formulations.

SUMMARY

The technical solution in accordance with the present invention provides one chlorogenic acid powder for injection, and another technical solution in accordance to the present invention provides the preparative method for an injection-use chlorogenic acid powder.

The present invention provides one injection-use chlorogenic acid powder, and it is prepared at a proportion by weight from the following raw materials:

1-120 parts of chlorogenic acid, 1-320 parts of a supporting material, and 1-8 parts of an antioxidant.

In which, said supporting materials are selected from the group consisting of sucrose, mannitol, glucose, lactose, trehalose, hetastarch, dextran 20, sorbitol, PEG1000, glycerol, glycine, 1,2-propylene glycol, and mixtures thereof; said antioxidants are selected from the group consisting of sodium bisulfite, sodium pyrosulfite, L-cysteine hydrochlorate, or vitamin C, and mixtures thereof.

In which, said supporting material is mannitol; said antioxidant is sodium bisulfite.

In which, the purity of said chlorogenic acid is above 98%.

In which, the formulations are prepared at a proportion by weight from the following raw materials:

1-120 parts of chlorogenic acid, 1-320 parts of a supporting material, and 1-8 parts of an antioxidant.

Further preferably, the formulation is prepared at a proportion by weight from the following raw materials:

30 parts of chlorogenic acid, 2 parts of sodium bisulfite, and 80 parts of mannitol.

The present invention also provides the preparative method for said powder injection, that includes the following specific steps:

a. Taking appropriate amount of chlorogenic acid, sodium bisulfite, and mannitol, and then accurately weighing their masses, respectively;

b. Taking suitable amounts of water for injection, then successively adding sodium bisulfite, chlorogenic acid, and mannitol; thoroughly dissolving by stirring; adjusting pH value to 2-4; the temperature of water for injection is 45-50° C.; adding 0.03% of activated carbon and stirring for 30 minutes; filtering out the activated carbon, then filtering the filtrate via 0.22 μm hydrophilic microporous membranes, to obtain clear solution; canning the filtered filtrate into a vial; and aseptically feeding into a lyophilizer, to obtain lyophilized powder.

In which, said lyophilized process includes the following specific steps: cooling to −38° C. and thermally-insulating for 3 hours, with the temperature of condenser at −60° C.; then gradually warming to a temperature between −45° C. and −23° C. in 12 hours; subsequently warming to a temperature between −23° C. and −28° C. in 6.5 hours. The initial degree of vacuum is 400-450 mbar, while the end degree of vacuum is 180-200 mbar, with the lowest degree of vacuum of 180 mbar. The freeze dehydration takes 24 hours, and secondary drying is carried out at +30° C. for 3 h.

In which, as mentioned in step b, the phosphate buffered solution is added to adjust pH value to 3-3.5.

In which, said packing materials are brown injection vials made of molded low borosilicate glass, as well as pharmaceutically acceptable butyl rubber bottle plug.

The powder injections according to the present invention have the following advantages: 1. Chlorogenic acid is an instable polyphenol compound, and susceptible to be affected by digestive tract bacteria and so on. If using its injection preparations, as for pharmacotherapy, the biological availability will be high, and its application will have a fast effect; chlorogenic acid is not stable in aqueous solution, but its lyophilized powder for injection can avoid the degradation of chlorogenic acid in water. 2. A fast therapeutic effectiveness: Injections can be directly administrated into the human body tissues, thus leading to a quick absorption and a quick action. Especially for intravenous injections, drugs can directly enter into blood vessels without absorption stage, and injection is superior for its fastest action among all formulations. 3. Accurate dosage and reliable functions: injections are administrated by parenteral route, and cannot be influenced by gastrointestinal tract factors, so have advantages of accurate dosage and reliable functions. 4. Fit for patients unable to take orally. The injection-use chlorogenic acid powder according to the present invention has the advantages of good stability, good solubility, and safe application in clinic.

EMBODIMENTS

Example 1 Selection Trial of Adjuvants for the Injection-Use Chlorogenic Acid Powder Experiments on the crude drug solubility of chlorogenic acid indicated samples are freely soluble in methanol and ethanol, soluble in acetone, and very slightly soluble in ethyl acetate; and its solubility in water was about 2%.

Results of experiments on hygroscopicity showed chlorogenic acid had hygroscopicity.

Results of experiments on stability of crude drugs showed chlorogenic acid was sensitive to light and heat.

Chlorogenic acid was a polyphenolic compound and may be easily oxidized, thereby, it should be considered whether antioxidants can be added into the formulation; the solubility of chlorogenic acid in water was about 2%, thus when the solution was prepared, its concentration should be controlled to less than 2%; for the hygroscopicity of chlorogenic acid, the ambient humidity of formulation research and production environment need be controlled; chlorogenic acid was sensitive to light, packing materials should be able to avoid light and directly contact with medicaments; chlorogenic acid was sensitive to heat, the temperature of technical process should be controlled.

1. Choosing Antioxidants

Chlorogenic acid possessed a polyphenolic structure, and can be easily oxidized and decomposed. In order to prevent oxidation of chlorogenic acid during its production and storage process, addition of antioxidants to the preparation formulation is necessary to be considered. Antioxidants, generally used in injections, included sodium bisulfite, sodium pyrosulfite, L-cysteine hydrochlorate, and vitamin C, et al., and their usual amounts were 0.1-0.2%. The antioxidants mentioned above were intended to be screened.

2. Choosing pH Regulators

Figure 1:
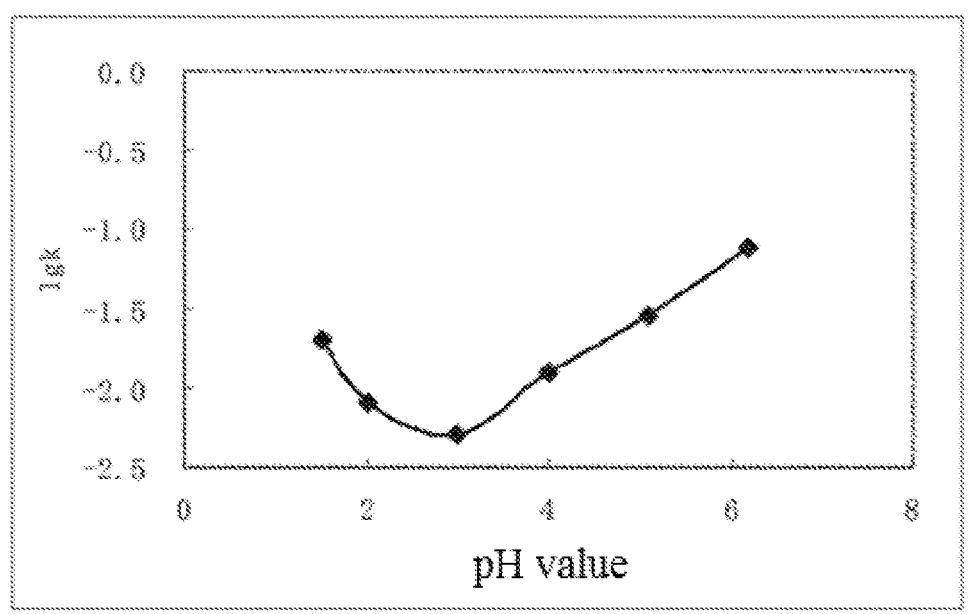
FIG. 1 shows the plot of pH-degradation reaction rate for chlorogenic acid.

There was a ester bond in the molecular structure of chlorogenic acid, and so pH values had an important effect on its hydrolytic degradation. The phosphate buffered solution is added to adjust pH value of chlorogenic acid formulations to 1.5-6.2. The degradation rate constant (k) of chlorogenic acid was determined, and then pH and its corresponding 1 gk were plotted to form a pH-1 gk curve and obtain constant $pH_m$ value. Results were shown in FIG. 1. The degradation of chlorogenic acid can be calculated according to first order kinetics (Seeing Tables 1 and 2, FIG. 1).

TABLE 1

Concentrations (μg/ml) of chlorogenic acid at different time points in buffer solutions with different pH values.

| pH | 0 h | 3 h | 7 h | 11 h | 17 h | 22 h |
|---|---|---|---|---|---|---|
| 1.5 | 108.07 | 97.95 | 92.20 | 78.65 | 76.80 | 68.79 |
| 2.0 | 108.42 | 98.91 | 97.79 | 99.67 | 90.77 | 88.26 |
| 3.0 | 107.51 | 103.02 | 101.91 | 102.01 | 96.77 | 95.18 |
| 4.0 | 106.38 | 100.68 | 95.78 | 91.29 | 85.09 | 80.21 |
| 5.1 | 105.96 | 97.99 | 88.87 | 81.70 | 66.59 | 55.83 |
| 6.2 | 105.67 | 67.91 | 43.91 | 33.46 | 22.91 | 18.48 |

TABLE 2

Results of linear regression, constants of reaction rate (k) and lgk under different pH values.

| pH | slope | intercept | R | constants of reaction rate k | lgk |
|---|---|---|---|---|---|
| 1.5 | −0.0198 | 4.6526 | −0.9763 | 0.0198 | −1.7036 |
| 2.0 | −0.0080 | 4.6557 | −0.9212 | 0.0080 | −2.0947 |
| 3.0 | −0.0051 | 4.6659 | −0.9635 | 0.0051 | −2.2931 |
| 4.0 | −0.0125 | 4.6557 | −0.9979 | 0.0125 | −1.9027 |
| 5.1 | −0.0288 | 4.6808 | −0.9955 | 0.0288 | −1.5412 |
| 6.2 | −0.0768 | 4.4716 | −0.9786 | 0.0768 | −1.1144 |

The above experimental results showed that as the increasing pH values, k values increased first and decreased afterwards, while the contents of chlorogenic acid decreased first and increased afterwards. According to the pH-degradation reaction rate curve, it can be seen that the aqueous solutions of chlorogenic acid with pH values of 2-4 were more stable, and the solution with a pH value of 3 was most stable. As a result, the pH value of prepared chlorogenic acid solution for injection was in the range of 2-4.

The proposed specification of chlorogenic acid formulation was 30 mg/injection, and in clinical practice, the pH value of solution with a higher concentration (0.03%) was about 3.5. The concentration of prepared chlorogenic acid solution was 1.5% before freeze-drying, and its pH value was about 3.0 according to pretesting. Both of pH values are in the range of 2-4, consequently, pH modifying agents were not considered being added when screening excipients used in the formulations.

3. Choosing Supporting Material for Freeze-Drying

Supporting materials were mainly used in lyophilized injections, and their uses allowed to produce uniform crystals of solid matter formed by freeze-drying. The obtained crystals had consistent color, an almost same volume with initial solutions, good dispersibility, without collapse and shrinkage. Commonly used supporting materials were mannitol, lactose, and glycine, etc., and thus different amounts of mannitol, lactose, and glycine were selected to carry out formulation screening.

4. Formulation Screening and Optimization 4.1 Screening and Optimizing of Antioxidants To the chlorogenic acid solution, was added sodium bisulfite, sodium pyrosulfite, L-cysteine hydrochlorate, and vitamin C in an amount of 0.1% by heating to boiling. The content change of chlorogenic acid was detected by HPLC method to determine the optimal antioxidant and its amount. Results were shown in Table 3.

TABLE 3

Effects of antioxidants on the stability of chlorogenic acid solution.

| | Peak area (percentage) | | |
|---|---|---|---|
| sample | 0 min | 75 min | 150 min |
| Control(without antioxidants) | 2542434 (100%) | 2238320 (88.0%) | 2124074 (83.5%) |
| Sodium bisulfite | 2532554 (100%) | 2410277 (95.2%) | 2349105 (92.8%) |
| Sodium pyrosulfite | 2568769 (100%) | 2263222 (88.1%) | 2114952 (82.3%) |
| L-cysteine hydrochlorate | 2580619 (100%) | 2359955 (91.4%) | 2317304 (89.8%) |
| Vitamin C | 2551027 (100%) | 2299927 (90.2%) | 2255217 (88.4%) |

When used in the experiment, the antioxidants sodium bisulfite, L-cysteine hydrochlorate, and vitamin C all can improve the stability of chlorogenic acid, but sodium pyrosulfite was not able to increase its stability; however, the color of chlorogenic acid solutions containing L-cysteine hydrochlorate and vitamin C turned dark, while addition of sodium bisulfite did not cause any effect on the solution color. It was reported that the antioxidation principle of sodium bisulfite was based on its higher standard potential ($E^0$), in other words, it was firstly oxidized and destroyed, compared with medicaments. At present, the parenteral solutions comprising sodium bisulfite as antioxidant included Etamsylate Injection, Metamizole Sodium Injection, Dexamethasone Sodium Phosphate Injection, and so on, and the amount of sodium bisulfite used in those injections ranged from 0.1% to 0.2%. Sodium bisulfite was a conventional antioxidant for injections, and had a higher safety to human. Moreover, sodium bisulfite and chlorogenic acid both were reducing substances, and could not produce reactions, thereby, they possessed better compatibility (Experiments on influencing factors of pilot products also proved the better compatibility). Therefore, 0.1% sodium bisulfite was selected as antioxidant and used in the product of present invention.

4.2 Screening and Optimizing of Supporting Materials

Varied amounts of mannitol, lactose, and glycine were selected as supporting materials, and compared based on the evaluation indexes including appearance, solubility (Observing after addition of 0.9% NaCl injection (2 ml)), and clarity, to screen out the best supporting materials and its dosage. Results were shown in Table 4.

TABLE 4

Effects of different supporting materials and their dosages on the lyophilized formulations

| Category | Appearance | Solubility | Clarity |
|---|---|---|---|
| Without supporting material | Imperfect full | ++++ | clear |
| 2% mannitol | Relative full, surface with holes | +++ | clear |
| 4% mannitol | Full, loose texture | ++++ | clear |
| 6% mannitol | Full, loose texture | ++ | clear |
| 8% mannitol | Full, loose texture | ++ | clear |
| 10% mannitol | Full, loose texture | ++ | clear |
| 2% lactose | Not full, surface with holes | +++ | turbid |
| 4% lactose | Not full, surface with holes | +++ | turbid |
| 6% lactose | Not full, surface with holes | +++ | turbid |
| 8% lactose | Not full, porous surface, nonuniform color | +++ | turbid |
| 1% glycine | Not full, with honeycomb holes | +++ | clear |
| 2% glycine | Not full, with honeycomb holes | +++ | clear |

Note:
"++++" indicates quick dissolution;
"+++" indicates not so fast dissolution, but presents block substances at begin;
"++" indicates slow dissolution, while presents block substances at begin.

Results showed using 4% mannitol as supporting materials afforded products with better moldability, solubility, and clarity. Mannitol was a general supporting material for lyophilized powder injection, and had a higher safety to human and a stable chemical property. It is difficult for mannitol to have a reaction with chlorogenic acid, and thus both of them should have a better compatibility (Experiments on influencing factors of pilot products also proved the better compatibility). Therefore, 4% mannitol was chosen as the supporting material for the production of present invention.

5. Determination of Formulation

According to above experimental results of screening out and optimizing formulations, for 1000 dosage units (30 mg/injection), the formulation was determined as follows:

| chlorogenic acid | 30 g | remedium cardinale |
|---|---|---|
| sodium bisulfite | 2 g | antioxidant |
| mannitol | 80 g | supporting material |
| water for injection to | 2000 ml | solvent |

1000 injections were prepared by freeze dry.

6. Experiment on Adjuvant Materials' Compatibility

Pure chlorogenic acid and chlorogenic acid containing adjuvants were tested under high temperature (60° C.), high humidity (relative humidity 92.5%) and bright light (intensity of light 4500 lx±500 lx), respectively, and the test items included description, loss on drying, related substances, and content.

6.1 High Temperature Test

Pure chlorogenic acid and the mixture of chlorogenic acid and adjuvants were placed in an incubator at a temperature of 60° C., and samples were taken and examined on 0, 5th, 10th days, respectively. Results were depicted in Table 5.

TABLE 5

Results of high temperature (60° C.) test

| Day | Sample | Description | Loss on drying (%) | Related substances (%) | | | | | | Content (%) |
| | | | | Caffeic acid | Others | | | | | |
| | | | | | 1 | 2 | 3 | 4 | Total | |
|---|---|---|---|---|---|---|---|---|---|---|
| 0 | Chlorogenic acid | Off-white crystal powder | 2.31 | 0.083 | 0.106 | 0.154 | 0.211 | 0.035 | 0.504 | 99.51 |
| | Chlorogenic acid containing adjuvants | Off-white powder | 1.67 | 0.079 | 0.106 | 0.155 | 0.203 | 0.030 | 0.494 | 99.57 |
| 5 | Chlorogenic acid | Dark brown lump | 2.25 | 0.104 | 0.134 | 0.160 | 0.294 | 0.039 | 0.627 | 99.36 |
| | Chlorogenic acid containing adjuvants | Dark brown powder | 0.52 | 0.107 | 0.125 | 0.165 | 0.261 | 0.030 | 0.580 | 99.42 |
| 10 | Chlorogenic acid | Dark brown lump | 2.13 | 0.121 | 0.143 | 0.175 | 0.306 | 0.047 | 0.670 | 99.31 |
| | Chlorogenic acid containing adjuvants | Dark brown powder | 0.60 | 0.116 | 0.128 | 0.164 | 0.258 | 0.034 | 0.584 | 99.41 |

For pure chlorogenic acid and chlorogenic acid containing adjuvants, compared with day 0, results indicated all test items including description, loss on drying, related substances, and content were almost identical after treatment at high temperature for respective five days and ten days, suggesting at high temperature (60° C.), adjuvants and chlorogenic acid had better compatibility.

6.2 High Humidity Test

Pure chlorogenic acid and chlorogenic acid containing adjuvants were respectively placed in a dryer under a relative humidity of 92.5% ($KNO_3$ saturated solution), and then moved an incubator at 25° C. for observation. Samples were taken and examined on 0, 5th, 10th days, respectively, and results were depicted in Table 6.

stances, and content were almost identical after treatment at high humidity for respective five days and ten days, suggesting adjuvants and chlorogenic acid had better compatibility under high humidity.

6.3 Bright Light Exposure Test

Pure chlorogenic acid and chlorogenic acid containing adjuvants were placed in an illumination incubator with an illumination intensity of 4500±500 lx at ambient temperature for test. Samples were taken and examined on 0, 5th, 10th days, respectively, and results were depicted in Table 7.

TABLE 6

Results of high humidity (92.5% relative humidity) test

| Day | Sample | Description | Loss on drying (%) | Caffeic acid | Related substances (%) 1 | 2 | 3 | 4 | Total | content (%) |
|---|---|---|---|---|---|---|---|---|---|---|
| 0 | Chlorogenic acid | Off white crystal powder | 2.31 | 0.083 | 0.106 | 0.154 | 0.211 | 0.035 | 0.504 | 99.51 |
|   | Chlorogenic acid | Off white powder | 1.67 | 0.079 | 0.106 | 0.155 | 0.203 | 0.030 | 0.494 | 99.57 |
| 5 | Chlorogenic acid | Pale yellow lump | 4.22 | 0.102 | 0.123 | 0.157 | 0.203 | 0.036 | 0.518 | 99.47 |
|   | Chlorogenic acid | Off white lump | 8.35 | 0.101 | 0.125 | 0.154 | 0.204 | 0.033 | 0.516 | 99.46 |
| 10 | Chlorogenic acid | Pale yellow lump | 4.75 | 0.103 | 0.135 | 0.174 | 0.221 | 0.041 | 0.570 | 99.43 |
|   | Chlorogenic acid | Off white lump | 8.52 | 0.104 | 0.127 | 0.171 | 0.211 | 0.038 | 0.547 | 99.45 |

For pure chlorogenic acid and chlorogenic acid containing adjuvants, compared with day 0, results indicated all test items including description, loss on drying, related sub-

TABLE 7

Results of bright light (light intensity 4500 lx ± 500 lx) exposure test

| Day | Sample | Description | Loss on drying (%) | Caffeic acid | Related substances (%) Others 1 | 2 | 3 | 4 | Total | Content (%) |
|---|---|---|---|---|---|---|---|---|---|---|
| 0 | Chlorogenic acid | Off white crystal powder | 2.31 | 0.083 | 0.106 | 0.154 | 0.211 | 0.035 | 0.504 | 99.51 |
|   | Chlorogenic acid containing adjuvants | Off white powder | 1.67 | 0.079 | 0.106 | 0.155 | 0.203 | 0.030 | 0.494 | 99.57 |
| 5 | Chlorogenic acid | Dark brown lump | 2.38 | 0.102 | 0.129 | 0.483 | 0.223 | 0.037 | 0.871 | 99.15 |
|   | Chlorogenic acid containing adjuvants | Pale yellow powder | 0.94 | 0.109 | 0.127 | 0.470 | 0.220 | 0.031 | 0.848 | 99.15 |
| 10 | Chlorogenic acid | Dark brown lump | 2.54 | 0.116 | 0.129 | 0.498 | 0.235 | 0.044 | 0.905 | 99.07 |
|   | Chlorogenic acid containing adjuvants | Pale yellow powder | 0.63 | 0.112 | 0.127 | 0.495 | 0.232 | 0.042 | 0.896 | 99.10 |

For pure chlorogenic acid and chlorogenic acid containing adjuvants, compared with day 0, results indicated all test items including description, loss on drying, related substances, and content were almost identical after exposure to bright light for respective five days and ten days, suggesting adjuvants and chlorogenic acid had better compatibility under bright light.

Test results of pure chlorogenic acid and chlorogenic acid containing adjuvants under high temperature, high humidity and bright light showed adjuvants and chlorogenic acid had good compatibility.

Example 2 Technical Study of Chlorogenic Acid Powder for Injection According to the Present Invention Based on the dosage form characteristics of lyophilized powder for injection and the physico-chemical property of crude drug chlorogenic acid, technical design and technical study of injection-use chlorogenic acid were carried out.

1. Technical Design

Figure 2:
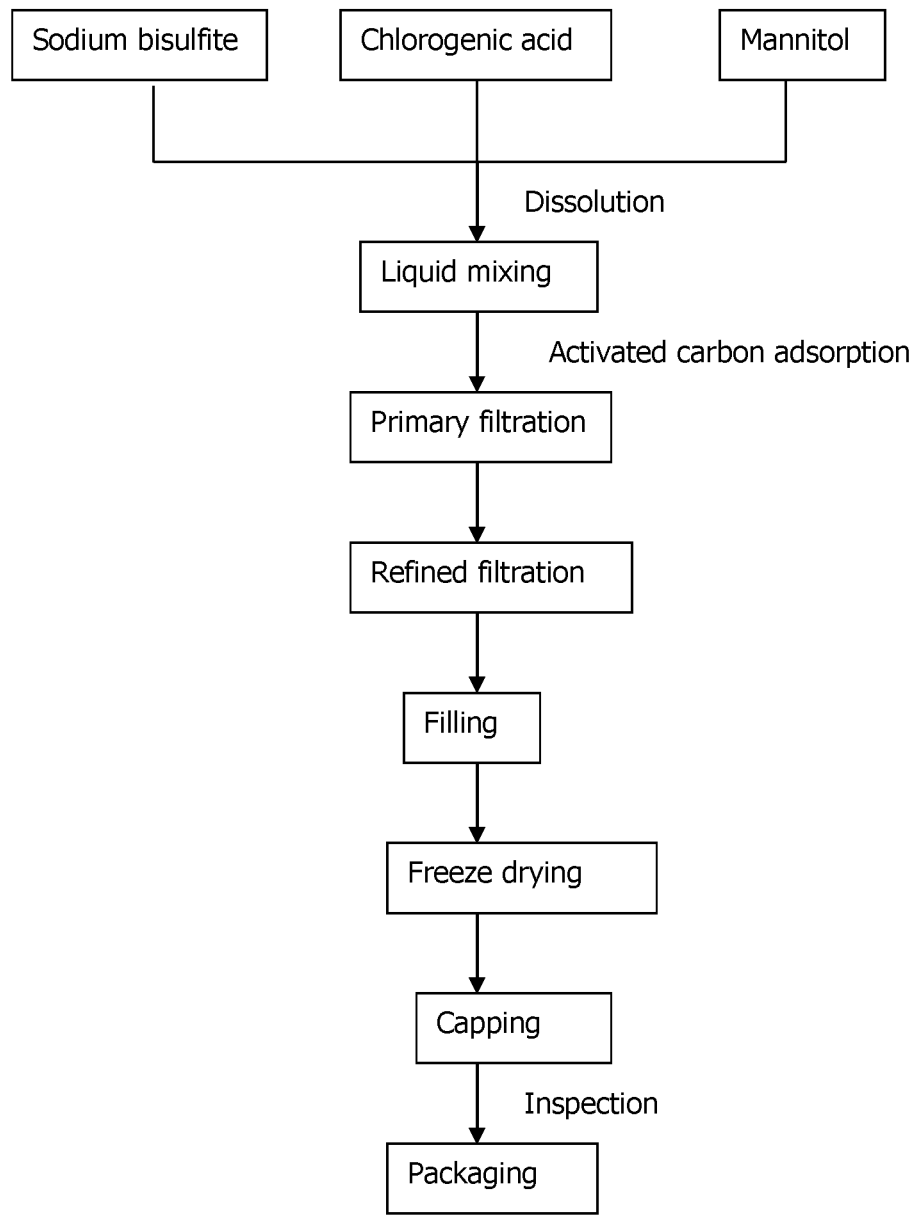
FIG. 2 shows the flow chart of preparative technology.

The technical process of injection-use chlorogenic acid was designed as: preparing solution→aseptic filtration→aseptic canning→freeze drying→packaging, and the technical flow chart for production was depicted in FIG. 2.

2. Technical Study 2.1 Technical Study of Preparing Solution (1) Technical Study of Solution As the order of materials input, the antioxidant sodium bisulfite was firstly added, and dissolved with water for injection, then chlorogenic acid was added and dissolved. The supporting material mannitol was finally added and dissolved under stirring.

The dissolubility of chlorogenic acid in water was about 2%, and its concentration in the prepared solutions (about 1.5%) was lower than the dissolubility. Thus, the chlorogenic acid should be totally dissolved at ambient temperature, and the total solution was confirmed by experiments.

(2) Technical Study of Activated Carbon Adsorption

Activated carbon was a commonly used adsorbent for injection preparation, and the existence of numerous micropores in the particle interior warranted the activated carbon had a very large active surface, and the ability to adsorb pigments, impurity, and pyrogens in drug solution. The amount of activated carbon used was generally 0.01%-0.5%, such as the amount of activated carbon used in metronidazole injection usually was 0.05%-0.08%; the amount of activated carbon used in norfloxacin injection usually was 0.02%-0.04%; the amount of activated carbon used in mannitol injection usually was 0.2%-0.5%. In order to adequately ensure the formulation safety, the activated carbon was applied to adsorb pigments, impurity, and pyrogens in drug solution. However, if more activated carbon was added, the adsorption amount became larger, while more chlorogenic acid was lost. Thus, the usage amount of activated carbon was screened, and results were depicted in Table 8.

TABLE 8

Screening the amount of use of activated carbon

| Amount of use | Peak area of chlorogenic acid after absorption of 30 min | Relative amount of chlorogenic acid |
| --- | --- | --- |
| 0 | 2430905 | 100% |
| 0.01% | 2348778 | 96.60% |
| 0.03% | 2260966 | 93.0% |
| 0.05% | 2222165 | 91.4% |
| 0.10% | 2199387 | 90.5% |
| 0.20% | 2040291 | 83.9% |

The above results indicated as the amount of activated carbon was increased, the content of chlorogenic acid lowered. Under the conditions of not affecting adsorptive effect, it's better for less activated carbon to be used. Based on an overall consideration, we chose 0.03% of activated carbon. The absorptive time was 30 min, and the temperature of water for injection was 45-50° C. Bacterial endotoxin detection of experimental batch and pilot batch proved this procedure could effectively remove pyrogens.

(3) Primary Filtration Technology

After activated carbon was added and kept for 30 min, primary filtration was performed using filter paper, to remove activated carbon and ensure the effects of precision filtration. It was confirmed that the solution was clear after primary filtration.

2.2 Technical Study of Precision Filtration

Chlorogenic acid was sensitive to heat, and in order to adequately ensure the potency of chlorogenic acid, the technology of precision filtration was used to remove bacteria and impurities existed in final products. 0.22 μm microporous membrane was generally used to perform precision filtration. The product was an aqueous solution, and thus 0.22 μm hydrophilic microporous membrane was chosen to carry out the technical study of precision filtration. For precision filtration process, the reliability of membrane was investigated using the membrane integrity as indicator; the chlorogenic acid absorbency of membrane was investigated, using after precision filtration, the adsorption rate of chlorogenic acid as indicator; the technology practicability was investigated by sterility test, clarity and color, as well as visible foreign matters of drug solutions obtained after precision filtration.

(1) Investigation on Integrity of Filtration Membrane

Before and after precision filtration, 0.22 μm hydrophilic microporous membrane (Shanghai Ya Dong nuclear grade resin Co., Ltd) was subjected to bubble point test. Results showed before precision filtration, the accepted membrane pressure at bubble point was 0.40 Mpa, while after precision filtration, the accepted membrane pressure at bubble point was 0.41 Mpa. The membrane both had good integrity before and after precision filtration, indicating this microporous membrane can be used for removal of bacteria and impurity in the chlorogenic injection.

(2) Investigation of Chlorogenic Acid Absorbency of Filtration Membrane 0.22 μm hydrophilic microporous membrane (Shanghai Ya Dong nuclear grade resin Co., Ltd) was investigated on the chlorogenic acid absorbency, and results were depicted in Table 9.

TABLE 9

Results of absorbency test

| Content of chlorogenic acid (mg/ml) in solution before filtration | Content of chlorogenic acid (mg/ml) in solution after filtration | Adsorption rate (%) |
|---|---|---|
| 1.223 | 1.221 | 0.15 |
| 1.225 | 1.221 | 0.30 |
| 1.221 | 1.219 | 0.15 |

Results indicated that using 0.22 μm hydrophilic microporous membrane (Shanghai Ya Dong nuclear grade resin Co., Ltd), the absorption rate of chlorogenic acid was less, suggesting the microporous membrane can not cause larger loss of chlorogenic acid.

(3) Investigation on Related Quality Indicators of Fine Filtrate

TABLE 10

Test results of related quality indicators of fine filtrate

| No. | Sterility test | Clarity and color | visible foreign matters |
|---|---|---|---|
| 1 | Meet specification | Pale yellow clear solution | Not detected |
| 2 | Meet specification | Pale yellow clear solution | Not detected |
| 3 | Meet specification | Pale yellow clear solution | Not detected |

Results indicated that the use of 0.22 μm hydrophilic microporous membrane (Shanghai Ya Dong nuclear grade resin Co., Ltd) for precision filtration can effectively remove bacteria and foreign matters in drug solution, accompanied by less loss of chlorogenic acid.

2.3 Technical Study of Freeze-Drying

Chlorogenic acid was sensitive to heat, and thus the lyophilization technology was used in the production process. Chlorogenic acid was more stable under the conditions of low temperature. Moreover, for the drug solution, the solid content was not high, together with the low viscosity, and thus conventional freeze-drying conditions were used for the technical study. Pretesting conditions of freeze drying were designed and included pre-freezing temperature of −38° C., pre-freezing time of 3 hours, the condenser temperature of −60° C., and sublimation drying time of 24 hours.

TABLE 11

Pretesting results of freeze-dry technology

| Items | Results |
|---|---|
| Appearance | Full, loose texture |
| solubility | Quick solution |
| Clarity and color | Clear, colorless |
| Loss on drying | 2.86% |

Pretesting results of freeze-dry technology indicated the appearance, the solubility, and loss on drying, etc., all are better, and thus for the product, the pre-freezing temperature was determined as −38° C.; the pre-freezing time as 3 hours; the condenser temperature as −60° C.; the initial vacuum degree as 400-450 mbar, the end vacuum degree as 180-200 mbar, and the lowest vacuum degree as 180 mbar; and the sublimation drying time as 24 hours.

TABLE 12

Technical study of seven batches of products (technological parameters of freeze drying)

| Parameters | 1 | 2 | 3 | 4 | 5 | 6 | 7 |
|---|---|---|---|---|---|---|---|
| Pre-freezing temperature(° C.) | −38 | −38 | −38 | −38 | −38 | −38 | −38 |
| Pre-freezing time (h) | 3 | 3 | 3 | 3 | 3 | 3 | 3 |
| Warming(−45° C.--23° C.)time | 12 h | 12 h | 12 h | 12 h | 12 h | 12 h | 12 h |
| Warming(−23° C.-28° C.)time | 6.5 h | 6.5 h | 6.5 h | 6.5 h | 6.5 h | 6.5 h | 6.5 h |
| Condenser temperature | −60° C. | −60° C. | −60° C. | −60° C. | −60° C. | −60° C. | −60° C. |
| Initial vacuum degree | 9.1 Pa | 9.1 Pa | 9.1 Pa | 9.1 Pa | 9.1 Pa | 9.1 Pa | 9.1 Pa |
| End vacuum degree | 15.1 Pa | 15.1 Pa | 15.1 Pa | 15.1 Pa | 15.1 Pa | 15.1 Pa | 15.1 Pa |
| Lowest vacuum degree | 33.5 Pa | 33.5 Pa | 33.5 Pa | 33.5 Pa | 33.5 Pa | 33.5 Pa | 33.5 Pa |
| Secondary drying temperature | 30° C. | 30° C. | 30° C. | 30° C. | 30° C. | 30° C. | 30° C. |
| Secondary drying time | 3 h | 3 h | 3 h | 3 h | 3 h | 3 h | 3 h |

2.4 Investigation on Moisture Absorption of Freeze-Dry Products

Three injection-use chlorogenic acid lyophilized powder of about 0.5 g were placed in weighing bottles, respectively, and accurately weighed, then moved to dryer under relative humidity of 57.7% (25° C.). The sample bottles were weighed as schedule time, to calculate the average weight-gain percentage, and the hygroscopicity curve was drawn. Results were depicted in Table 13 and FIG. 3.

TABLE 13

The weight-gain percentage of injection-use chlorogenic acid

| Time | No. 1 | No. 2 | No. 3 | mean |
|---|---|---|---|---|
| 0 h | — | — | — | — |
| 4 h | 3.60% | 3.93% | 3.57% | 3.70% |
| 16 h | 4.48% | 4.48% | 4.53% | 4.50% |
| 23 h | 4.51% | 4.48% | 4.52% | 4.50% |
| 40 h | 4.51% | 4.49% | 4.53% | 4.51% |

Figure 3:
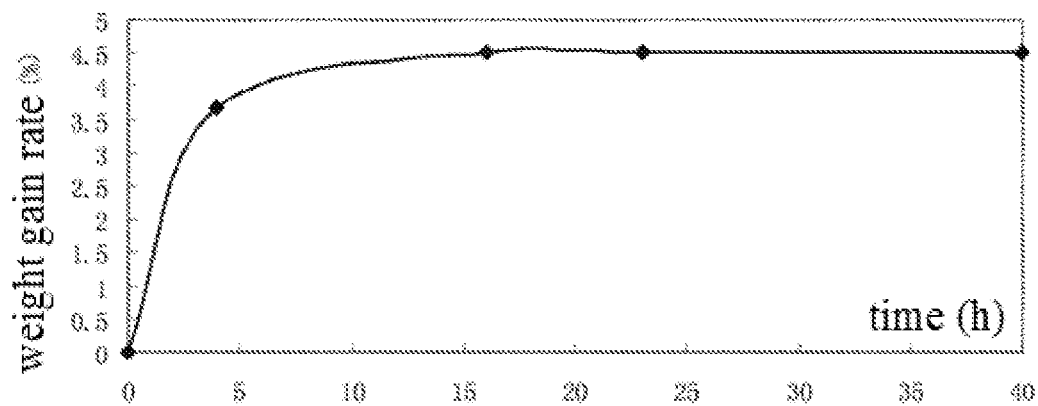
FIG. 3 shows the curve diagram of moisture equilibrium for chlorogenic acid.

In FIG. 3, it can be seen that when the injection-use chlorogenic acid was placed under the relative humidity of 57.7%, the weight gain was obvious within 4 hours, and then become flat. Thus, capping need finish after completion of freeze-drying.

2.5 Temperature-Time Freeze-Drying Curve of Lyophilized Product

Figure 4:
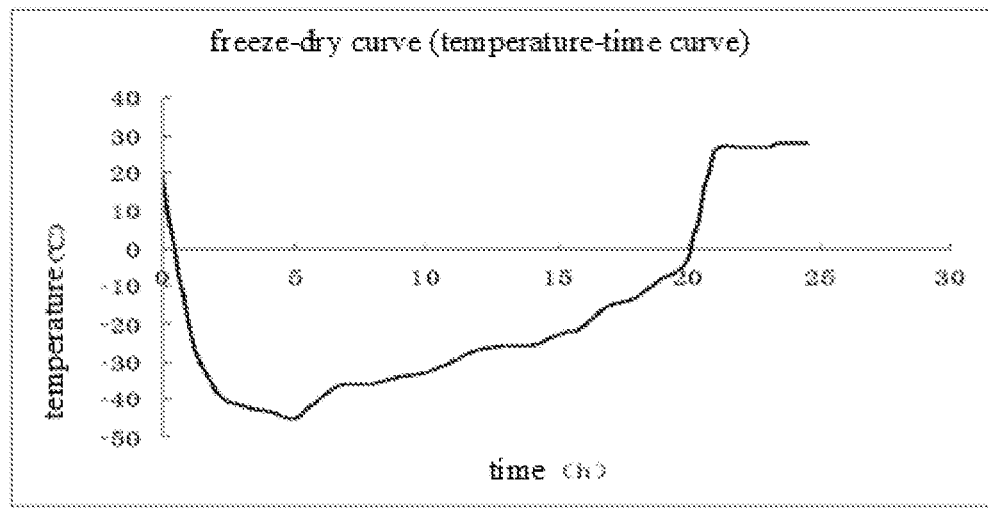
FIG. 4 shows the freeze-dry curve (temperature-time curve).

The freeze-drying curve reflected the time-variation of material temperature, baffle temperature, condenser temperature, and vacuum degree of box. Drawing freeze-drying curve can not only reflect the performance of freeze dryer, but also have some directive meaning toward practical production, seeing FIG. 4.

3. Technology Validation

Based on above results of technical study, the production technology of injection-use chlorogenic acid was determined as follows. According to the preparation formulation, the technology validation was performed using 125 injections per batch. To water for injection, were added successively sodium bisulfite, chlorogenic acid, and mannitol, and then allowed to totally dissolve by stirring, with a pH range of 2-4. 0.03% of injection-use activated carbon was added and stirred for 30 min, then the activated carbon was filtered out. After that, the precision filtration was performed using 0.22 μm microporous membrane to obtain clear filtrate, that was aseptically canned. The sample was lyophilized as the determined freeze-dry technology parameters, and capped to obtain products.

4. Preliminary Selection of Package Materials Contacting with Medicaments

Because chlorogenic acid was sensitive to light, packing materials, directly contacting with medicaments, should be able to avoid light, and thus brown injection vials made of molded low borosilicate glass, as well as pharmaceutically acceptable butyl rubber bottle plug, were preliminarily determined as the packing materials, directly contacting with medicaments.

5. Test of Influential Factors

Injection-use chlorogenic acid was placed in constant incubator at a temperature of 60° C. under relative humidity of 92.5%, as well as an incubator at a temperature of 25° C. and a light incubator with a illumination intensity of (4500±500)lx, respectively. On day 5th and on day 10th, the samples were taken out for detection of appearance, description, solution color, pH value, particulate matter, visible foreign matter, clarity, related substance, and labelled amount, together with the detection of exterior and interior surface characteristics of packing materials, i.e. brown injection vials made of molded low borosilicate glass, as well as pharmaceutically acceptable butyl rubber bottle plug, compared with the sample of day 0. Results were shown in the following:

TABLE 14

Test results of injection-use chlorogenic acid at high temperature, high humidity, and bright light.

| Factors | Day | Appearance | pH | Particulate matter | Visible foreign matter | Clarity and color | Related substances (%) Caffeic acid | Related substances (%) Others | Labelled content(%) |
|---|---|---|---|---|---|---|---|---|---|
| High temperature 60° C. | 0 | Off-white powder | 3.55 | Meet specification | Not detected | Clear, colorless | 0.230 | 0.474 | 99.45 |
|  | 5 | Pale-yellow powder | 3.57 | Meet specification | Not detected | Clear, colorless | 0.245 | 0.591 | 99.31 |
|  | 10 | Pale-yellow powder | 3.56 | Meet specification | Not detected | Clear, colorless | 0.280 | 0.699 | 99.19 |
| High humidity | 5 | Off-white powder | 3.54 | Meet specification | Not detected | Clear, colorless | 0.229 | 0.502 | 99.42 |
|  | 10 | Off-white powder | 3.53 | Meet specification | Not detected | Clear, colorless | 0.232 | 0.511 | 99.43 |
| Light | 5 | Off-white powder | 3.56 | Meet specification | Not detected | Clear, colorless | 0.250 | 0.649 | 99.23 |
|  | 10 | Off-white powder | 3.54 | Meet specification | Not detected | Clear, colorless | 0.269 | 0.674 | 99.07 |

Compared with day 0, after keeping at high temperature for 10 days, results showed that description of injection-use chlorogenic acid changed from off-white powder to pale-yellow powder; pH values were nearly not changed; the content of related substance caffeic acid increased by 21.74%, while the content of other substances increased by 47.47%; the content of chlorogenic acid decreased by 0.26%; appearance of brown injection vials made of molded low borosilicate glass, as well as pharmaceutically acceptable butyl rubber bottle plug both was not changed. Above results indicated high temperature had certain effect on the stability of injection-use chlorogenic acid, using brown injection vials made of molded low borosilicate glass, as well as pharmaceutically acceptable butyl rubber bottle plug as packaging materials, and the effect was almost equal to the test results of adjuvants' compatibility (without inner packaging) for chlorogenic acid containing adjuvants.

Compared with day 0, after keeping under high humidity for 10 days, results showed that description of injection-use chlorogenic acid was not changed on the whole; pH values were nearly not changed; the visible foreign matters were basically not changed; the contents of related substances were basically not changed; the content of chlorogenic acid was basically not changed; appearance of brown injection vials made of molded low borosilicate glass, as well as pharmaceutically acceptable butyl rubber bottle plug both was not changed. Above results indicated high humidity nearly did not have any effect on the stability of injection-use chlorogenic acid, using brown injection vials made of molded low borosilicate glass, as well as pharmaceutically acceptable butyl rubber bottle plug as packaging materials.

Compared with day 0, after keeping under bright light for 10 days, results showed that description of injection-use chlorogenic acid was not changed on the whole; pH values were nearly not changed; the visible foreign matters were basically not changed; the content of related substance caffeic acid increased by 16.96%, while the content of other substances increased by 42.19%; the content of chlorogenic acid on day 10th decreased by 0.38%, compared with day 0; appearance of brown injection vials made of molded low borosilicate glass, as well as pharmaceutically acceptable butyl rubber bottle plug both was not changed. Above results indicated bright light had certain effect on the stability of injection-use chlorogenic acid, using brown injection vials made of molded low borosilicate glass, as well as pharmaceutically acceptable butyl rubber bottle plug as packaging materials, and the effect was less than the test results of adjuvants' compatibility (without inner packaging) for chlorogenic acid containing adjuvants.

Above results showed high temperature and bright light had certain effect on the stability of injection-use chlorogenic acid, while high humidity nearly did not have effects on the stability of injection-use chlorogenic acid. The injection-use chlorogenic acid should be stored at cool and dark place, that used brown injection vials made of molded low borosilicate glass, as well as pharmaceutically acceptable butyl rubber bottle plug as packaging materials.

6. Stability Study on the Compatibility of Injection-Use Chlorogenic Acid

As the maximum concentration (0.03%) intended to be used in clinic, the injection-use chlorogenic acid was added with 0.9% sodium chloride injection, 5% glucose injection, and water for injection, respectively, to prepare test solution. Samples were taken at 0, 2, 4, and 6 hours, to inspect color, pH, clarity, particulate matter, visible foreign matter, related substances, labeled content, and other items of each test solution. Test results were shown in Table 15.

Test results indicated when the solution of injection-use chlorogenic acid was prepared at the maximum concentration intended to be used in clinic, using 0.9% sodium chloride injection, 5% glucose injection, and water for injection commonly used in clinic, the content of chlorogenic acid was not obviously changed in six hours; the solution was clear and colorless; Particulate matters and visible foreign matters meet specification; related substances were not obviously changed. These showed injection-use chlorogenic acid had a good compatibility with routine injection-use solvent in clinic. To ensure the quality of chlorogenic acid and its safety of administration, the prepared solution should be used in six hours after its preparation.

TABLE 15

Results of stability study on the compatibility of injection-use chlorogenic acid

| Solvents | Time (h) | pH | Clarity and color | Particulate matter | Visible foreign matter | Caffeic acid(%) | Related substances(%) 1 | 2 | 3 | 4 | 5 | 6 | Sum | Labelled Content (%) |
|---|---|---|---|---|---|---|---|---|---|---|---|---|---|---|
| 0.9% sodium chloride | 0 | 3.45 | Clear, colorless | Meet specification | Not detected | 0.011 | 0.047 | 0.062 | 0.015 | 0.082 | 0.031 | 0.238 | 0.475 | 99.52 |
| | 2 | 3.47 | Clear, colorless | Meet specification | Not detected | 0.013 | 0.045 | 0.050 | 0.013 | 0.077 | 0.031 | 0.206 | 0.422 | 99.42 |
| | 4 | 3.45 | Clear, colorless | Meet specification | Not detected | 0.010 | 0.044 | 0.018 | 0.022 | 0.047 | 0.039 | 0.239 | 0.409 | 99.47 |
| | 6 | 3.49 | Clear, colorless | Meet specification | Not detected | 0.010 | 0.041 | 0.033 | 0.020 | 0.048 | 0.044 | 0.239 | 0.425 | 98.93 |
| 5% glucose injection | 0 | 3.42 | Clear, colorless | Meet specification | Not detected | 0.025 | 0.016 | 0.028 | 0.061 | 0.022 | 0.022 | 0.272 | 0.421 | 99.46 |
| | 2 | 3.44 | Clear, colorless | Meet specification | Not detected | 0.025 | 0.013 | 0.024 | 0.056 | 0.011 | 0.022 | 0.297 | 0.423 | 99.10 |
| | 4 | 3.45 | Clear, colorless | Meet specification | Not detected | 0.016 | 0.011 | 0.024 | 0.060 | 0.010 | 0.020 | 0.312 | 0.437 | 98.87 |
| | 6 | 3.48 | Clear, colorless | Meet specification | Not detected | 0.020 | 0.010 | 0.020 | 0.045 | 0.015 | 0.025 | 0.274 | 0.389 | 99.04 |
| Sterile water for injection | 0 | 3.50 | Clear, colorless | Meet specification | Not detected | 0.037 | 0.014 | 0.028 | 0.054 | 0.022 | 0.118 | 0.229 | 0.465 | 99.66 |
| | 2 | 3.51 | Clear, colorless | Meet specification | Not detected | 0.041 | 0.016 | 0.024 | 0.057 | 0.019 | 0.123 | 0.238 | 0.477 | 99.33 |
| | 4 | 3.51 | Clear, colorless | Meet specification | Not detected | 0.036 | 0.016 | 0.025 | 0.059 | 0.023 | 0.221 | 0.245 | 0.589 | 99.10 |
| | 6 | 3.50 | Clear, colorless | Meet specification | Not detected | 0.038 | 0.011 | 0.016 | 0.047 | 0.016 | 0.278 | 0.185 | 0.553 | 99.07 |

In summary, in order to determine the reasonable formulations of injection-use chlorogenic acid, the present inventors made a screening for antioxidants, optimal pH value, the usage amount of activated carbon and its adsorption process, together with the supporting agents used in freeze-drying. Based on the screening results, sodium bisulfate was used as antioxidant; in the preparation process, pH values of chlorogenic acid were controlled in the range of 2-4, to keep the formulation stability; 0.03% of activated carbon was added and stirred for 30 min at 45° C.-50° C., then filtered out, while the loss percentage of chlorogenic acid was about 5%, and test results of pyrogen (endotoxin) meet the requirements; using 4% mannitol as supporting agents resulted in the formation of products with good moldability and good solubility; results of technical study proved the rationality of formulations and techniques; seven batches of products were manufactured and fully inspected, and their quality indicators all meet the specification, sufficiently proving the rationality of formulations and techniques. In addition, test results of influential factors of products indicated the injection-use chlorogenic acid should be stored at cool and dark place; investigation results of product quality and stability further proved the rationality of formulations and techniques; the stability study on compatibility of injection-use chlorogenic acid was carried out, and injection-use chlorogenic acid had a good compatibility with routine solvents used in clinic within six hours, thus the prepared solution was proposed being used in six hours after its preparation.

INDUSTRIAL APPLICATION

The injection-use powder of chlorogenic acid according to the present invention had the advantages of good stability, good solubility, safe application in clinic, and possessed a rather good prospects in clinical application and industrialization.

The invention claimed is:

1. A chlorogenic acid powder, comprising:
chlorogenic acid, a supporting material, and an antioxidant,
wherein the chlorogenic acid powder has a weight gain of about 4.5% based on a total weight of the chlorogenic acid powder after 16 hrs under a relative humidity of 57.7% at 25° C., and
wherein the chlorogenic acid powder is prepared by lyophilizing a solution containing, by weight proportions, 1-120 parts of the chlorogenic acid, 1-320 parts of the supporting material, and 1-8 parts of the antioxidant.

2. The chlorogenic acid powder according to claim 1, wherein the supporting material is selected from the group consisting of sucrose, mannitol, glucose, lactose, trehalose, hetastarch, dextran 20, sorbitol, PEG1000, glycerol, glycine, 1,2-propylene glycol, and mixtures thereof.

3. The chlorogenic acid powder according to claim 1, wherein the supporting material is mannitol and the antioxidant is sodium bisulfite.

4. The chlorogenic acid powder according to claim 2, wherein a purity of the chlorogenic acid is above 98%.

5. The chlorogenic acid powder according to claim 1, wherein the chlorogenic acid powder is prepared by lyophilizing a solution containing, by weight proportions, 30 parts of the chlorogenic acid, 2 parts of sodium bisulfite, and 80 parts of mannitol.

6. A method for preparing the chlorogenic acid powder of claim 1, comprising:
a. weighing appropriate amounts of chlorogenic acid, sodium bisulfite, and mannitol, respectively;
b. successively adding sodium bisulfate, chlorogenic acid, and mannitol in to a suitable amount of water of a temperature of 45-50° C. to form a solution; adjusting a pH value of the solution to 2-4; adding 0.03% of activated carbon into the solution and stirring for 30 minutes; filtering out the activated carbon from the solution, then filtering the filtrate using a 0.22 μm hydrophilic microporous membrane to obtain a clear solution; canning the clear solution in a vial; and lyophilizing the clear solution in the vial in a lyophilizer to obtain a lyophilized powder.

7. The method according claim 6, wherein the lyophilizing step comprises: freezing the clear solution at a temperature of −38° C. under a vacuum of 400-450 mbar for 3 hours; raising the temperature to between −45° C. and −23° C. in 12 hours; raising the temperature to between −23° C. and −28° C. in 6.5 hours; and maintaining said temperature for 24 hours under a vacuum of 180-200 mbar.

8. The method according claim 6, wherein, in said step (b) the pH value is adjusted to 3-3.5 using a phosphate buffer solution.

9. The method according claim 6, wherein said vial is made of molded low borosilicate glass, as well as and comprises a pharmaceutically acceptable butyl rubber bottle plug.

10. The chlorogenic acid powder according to claim 1, wherein the antioxidant is selected from the group consisting of sodium bisulfite, sodium pyrosulfite, L-cysteine hydrochlorate, vitamin C, and mixtures thereof.

11. The chlorogenic acid powder according to claim 1, having a pH value of about 3.5.

12. The chlorogenic acid powder according to claim 1, further comprising 0.2-0.3 wt % of caffeic acid based on a total weight of the chlorogenic acid powder.

13. The chlorogenic acid powder according to claim 1, wherein the lyophilizing the solution comprises freezing the solution at a temperature of −38° C. under a vacuum of 400-450 mbar for 3 hours; raising the temperature to between −45° C. and −23° C. in 12 hours; raising the temperature to between −23° C. and −28° C. in 6.5 hours; and maintaining said temperature for 24 hrs under a vacuum of 180-200 mbar.

14. A chlorogenic acid powder, comprising:
chlorogenic acid, a supporting material, and an antioxidant,
wherein the chlorogenic acid powder is prepared by a method that comprises:
weighing 1-120 parts of the chlorogenic acid, 1-320 parts of the supporting material, and 1-8 parts of the antioxidant;
successively adding chlorogenic acid, the supporting material, and the antioxidant in to a suitable amount of water of a temperature of 45-50° C. to form a solution;
adjusting a pH value of the solution to 2-4;
adding 0.03% of activated carbon into the solution and stirring for 30 minutes;
filtering out the activated carbon from the solution, then filtering the filtrate using a 0.22 μm hydrophilic microporous membrane to obtain a clear solution;
canning the clear solution in a vial; and
lyophilizing the clear solution in the vial in a lyophilizer to obtain a lyophilized powder.

* * * * *